United States Patent
Davis

(10) Patent No.: US 7,744,219 B2
(45) Date of Patent: Jun. 29, 2010

(54) BINOCULAR INDIRECT OPHTHALMOSCOPE FIXATION LIGHT

(76) Inventor: Andrew Peter Davis, 14360 SE. 47th Pl., Bellevue, WA (US) 98006

( * ) Notice: Subject to any disclaimer, the term of this patent is extended or adjusted under 35 U.S.C. 154(b) by 0 days.

(21) Appl. No.: 12/125,823

(22) Filed: May 22, 2008

(65) Prior Publication Data

US 2008/0291398 A1    Nov. 27, 2008

Related U.S. Application Data

(60) Provisional application No. 60/931,860, filed on May 26, 2007.

(51) Int. Cl.
*A61B 3/10* (2006.01)
(52) U.S. Cl. .................. 351/221; 351/243
(58) Field of Classification Search .............. 351/221
See application file for complete search history.

(56) References Cited

U.S. PATENT DOCUMENTS

| | | | | |
|---|---|---|---|---|
| 4,838,678 A | * | 6/1989 | Hubertus | 351/205 |
| 6,715,878 B1 | * | 4/2004 | Gobbi et al. | 351/243 |
| 7,425,067 B2 | * | 9/2008 | Warden et al. | 351/205 |
| 2005/0286019 A1 | * | 12/2005 | Wiltberger et al. | 351/211 |
| 2006/0050229 A1 | * | 3/2006 | Farberov | 351/161 |
| 2008/0044063 A1 | * | 2/2008 | Friedman et al. | 382/117 |

FOREIGN PATENT DOCUMENTS

| WO | WO2005017572 | 2/2005 |
|---|---|---|
| WO | WO2005094667 | 10/2005 |
| WO | WO2006041625 | 4/2006 |

* cited by examiner

*Primary Examiner*—Jessica T Stultz
(74) *Attorney, Agent, or Firm*—Black Lowe & Graham, PLLC

(57) ABSTRACT

A binocular indirect opthalmoscope assembly and fixation light system is disclosed for easily directing the patient's line of sight in a direction that places the optic nerve and surrounding vessels in the center of the examiner's view. The fixation system includes two fixation light assemblies that may be mounted onto the binocular indirect opthalmoscope assembly and activated by a motion sensor.

18 Claims, 3 Drawing Sheets

BINOCULAR INDIRECT OPHTHALMOSCOPE FIXATION LIGHT

PRIORITY CLAIM

This application claims the benefit of the filing date of U.S. Provisional Patent Application Ser. No. 60/931,860, filed May 26, 2007, which is herein incorporated by reference in its entirety.

BACKGROUND OF THE INVENTION

The indirect opthalmoscope is an instrument that is worn on an eye doctor's head like a helmet and enables the doctor or other examiner to examine a patient's retina. A light source directs coaxial illumination to facilitate the examiner's view of the retina through the patient's pupil. To use the indirect opthalmoscope, the examiner holds a special focusing lens in one hand near the patient's eye, and uses his other hand to hold the patient's eyelid open. One of the main goals during the retinal examination using the indirect opthalmoscope is to examine the patient's optic nerve and surrounding vessels. To center the optic nerve in the examiner's view, the patient needs to look more in the direction of the examiner's ear rather than at the light source. This is because the optic nerve is not in the visual center of the retina but rather about 15 degrees away from the center.

Thus, if the doctor is examining the patient's right eye, it is necessary for the patient to use his left eye (the eye being examined cannot see much because of the very bright light) to look in the direction of the doctor's right ear, which aligns the optic nerve with the examiner's view. The problem is that the room is usually dark for the examination, and there is a very bright light shining in one eye. This makes it extremely difficult to direct the patient's gaze toward any particular direction, and becomes frustrating for the patient as well as the physician.

There exists an unmet need in the art for a device that can readily direct the patient's gaze in the correct direction during the eye examination so that the doctor can easily see the patient's optic nerve and surrounding retinal vessels.

SUMMARY OF THE INVENTION

The present invention addresses the need for a device that can direct the patient's gaze during an eye examination so the examiner can easily see the patient's optic nerve and surrounding retinal vessels.

The binocular indirect opthalmoscope assembly of the present invention comprises a housing having a pair of eyepieces. The housing itself is removably attached to the head of the user so that, in doing so, one eyepiece registers with each eye. An illuminating light source is projected from the binocular indirect opthalmoscope along the viewing axis to illuminate the patient's retina. An optical system, typically comprising a pair of mirrors and a prism, is contained within the housing so that the light reflected back from the patient's eye directed to each eyepiece along the viewing axis. The present invention provides a plurality of fixation light assemblies mounted on either side of the binocular indirect opthalmoscope housing, specifically on the side of the right and left eyepieces of the eyepiece housing.

In one embodiment of the present invention, a binocular indirect opthalmoscope assembly includes: an eyepiece housing having a right and a left eyepiece; a means for removably securing the eyepiece housing to a head of a user; an illumination source to project a bright light along the optical viewing axis; an optical system contained in the eyepiece housing for reflecting light along an optical viewing axis to each of the eyepieces; and a binocular indirect fixation system comprising a plurality of fixation light assemblies, wherein a first fixation light mounted on a first fixation light assembly directs the patients direction of gaze so as to place the optic nerve and surrounding retinal vessels of the eye being examined in the center of the examiner's view, and a second fixation light mounted on a second fixation light assembly is hidden from view as the rotation of the viewing axis is turned toward the eye being examined, causing the fixation light housing to obstruct the view of the second fixation light. The second fixation light can be used in a similar fashion to the first fixation light during an examination of the opposite eye of the patient.

In another exemplary embodiment, each fixation light assembly includes a fixation light source mounted onto an external face of a fixation light housing, a motion/vibration sensor, a microprocessor, and a power source. The fixation light housing has two mounting sides. On a first and external mounting side, a fixation light source is mounted at right angles on the external face; on a second mounting side, the fixation light housing can be attached to the eyepiece housing of the binocular indirect opthalmoscope assembly.

In another exemplary embodiment, the plurality of fixation light assemblies can be activated by the motion sensing device mounted in the fixation light housing. Once the sensor detects motion of the binocular indirect opthalmoscope, it sends a signal to the microprocessor, also housed in the fixation light housing. The microprocessor, in communication with the motion sensing device, turns on the fixation light source in response to the motion detected by the motion sensing device. The power source, for example, a battery, is housed therein to power the light, the microprocessor and the motion sensing device. Alternatively, the plurality of fixation light assemblies can be connected by direct wiring to a power source.

In another exemplary embodiment, the binocular indirect fixation system includes an LED light source.

In a preferred embodiment of the invention described here, the binocular indirect opthalmoscope fixation light can be mounted on the binocular indirect opthalmoscope assembly. In an alternative embodiment, the fixation light assembly can be mounted with an adapter fitting to allow the fixation light assembly to be mounted onto a binocular indirect opthalmoscope assembly that has an eyepiece housing of insufficient size and/or orientation to allow proper alignment and or position of the fixation light assembly. For example, an adapter fitting might be a cap that fits over one end of the eyepiece housing adjacent to the eyepiece. The cap can have two ends: a first and open end slidably mounted onto the eyepiece housing, and a second mounting end to mount the fixation light assembly.

In another exemplary embodiment, the fixation light assembly can be built into the eyepiece housing of the binocular indirect opthalmoscope assembly.

In another exemplary embodiment, the fixation light assembly can be affixed to the binocular indirect opthalmoscope assembly; for example, to the head mounting apparatus close to the ears of the examiner, or to other parts of the binocular indirect opthalmoscope assembly other than the eyepieces.

These and other examples of the invention will be described in further detail below.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

The preferred and alternate embodiments of the present invention are better understood with reference to FIGS. 1-4.

Figure 1:
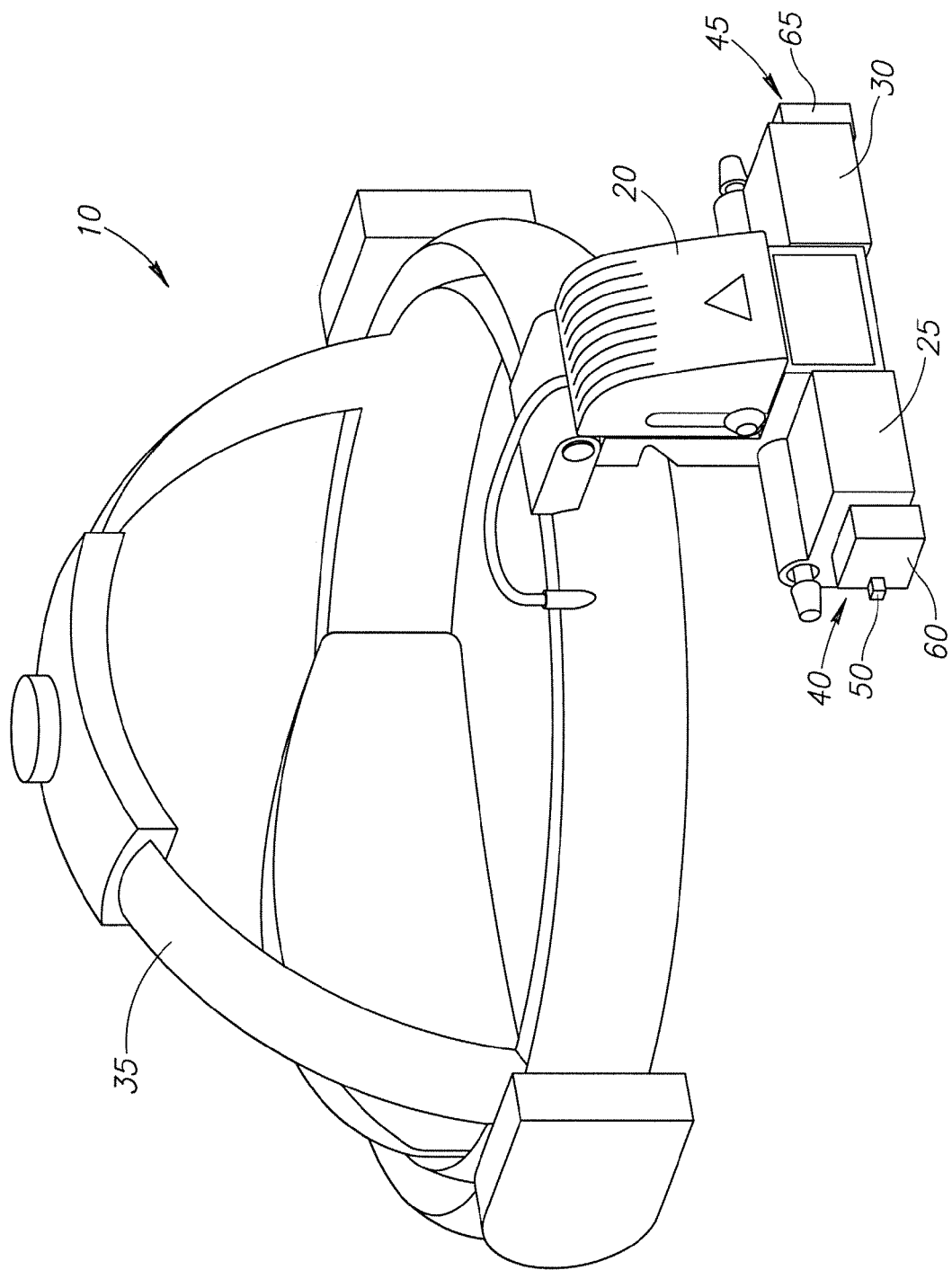
FIG. 1 shows two binocular indirect opthalmoscope fixation light assemblies mounted on the side of the right and left eyepieces of the binocular indirect opthalmoscope.
Figure 4:
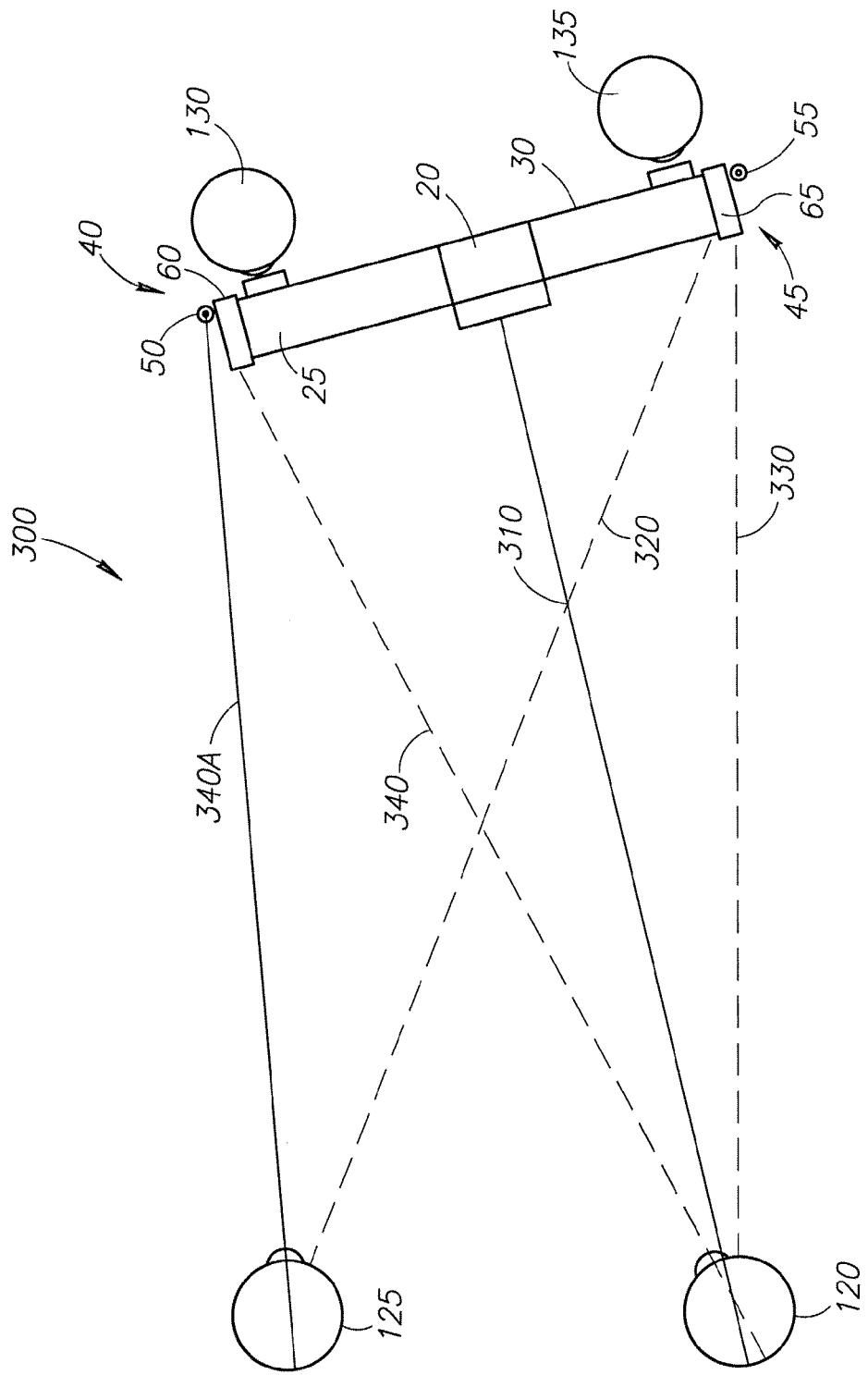
FIG. 4 shows a schematic diagram of the pathways of light of the binocular indirect opthalmoscope in use.

FIG. 1 illustrates a preferred embodiment of a binocular indirect opthalmoscope assembly 10 of the present invention. This embodiment comprises an opthalmoscope housing 20 having a right eyepiece 25 and a left eyepiece 30 and a means for removably securing the opthalmoscope housing to a head of a user, for example a head mounting apparatus 35. The eyepiece housing 20 is adapted to be detachably secured to the head of a user by using a head mounting apparatus 35 so that in use one eyepiece 25, 30 registers with each eye of the user (see FIG. 4). An illumination system is contained in the upper part of the eyepiece housing 20 and provides a means to direct a bright illumination light into the patient's eye being examined along the same path as the optical viewing axis (FIG. 4, 310). An optical system (not shown) contained in the eyepiece housing 20 reflects from the viewing axis (FIG. 4, 310) into each of the eyepieces of the examiner.

The binocular indirect fixation system 300, as exemplified and as further described in FIG. 4, includes a means to direct the patients direction of gaze so as to place the optic nerve and surrounding retinal vessels of the eye being examined in the center of the examiner's view. The system includes first and second fixation lights mounted on first and second fixation light assemblies. The first fixation light mounted on the first fixation light assembly directs the patient's direction of gaze so as to place the optic nerve and surrounding retinal vessels of the eye being examined in the center of the examiner's view. The second fixation light mounted on the second fixation light assembly is hidden from view as the rotation of the viewing axis is turned toward the eye being examined, causing the fixation light housing to obstruct the view of the second fixation light. The second fixation light can be used in a similar fashion to the first fixation light during an examination of the opposite eye of the patient.

With reference to FIG. 1, the plurality of fixation light assemblies 40, 45 are preferably mounted on either side of the eyepiece housing 20 so that they are positioned adjacent to each of the doctor's eyes. One fixation light assembly 40 is positioned on the right side adjacent to the right eyepiece 25, and another fixation light assembly 45 is positioned on the left side adjacent to the left eyepiece 30. Each fixation light assembly includes a fixation light 50, which is exemplified in FIG. 1 positioned adjacent to the right eyepiece and mounted onto the fixation light housings 60 at a right angle. A second fixation light assembly is positioned adjacent to the left eyepiece (obscured in this view). Each fixation light assembly may be detachably mounted by means of the self-adhesive strip (see FIG. 2, 80) or other similar attachment means, such as hook and loop fasteners, friction fittings, etc., and in such an orientation that the fixation light source 50, 55 is in communication with a printed circuit board 70, mounted on the fixation light housing 60, 65 (see FIG. 2, 70). The printed circuit board 70 is preferably oriented in a direction parallel to the optical viewing axis (see FIG. 4, 310) of the binocular indirect opthalmoscope assembly 10 and in the direction of the projected light from the light sources 50, 55.

In other exemplary embodiments, the fixation light assembly 40, 45 may be mounted using an adapter fitting (not shown) on a binocular indirect opthalmoscope assembly 10 that has an eyepiece housing 20 of insufficient size and/or orientation to allow proper alignment and or position of the fixation light assembly 40, 45. For example, an adapter fitting might be a cap that fits over one end of the eyepiece housing adjacent to the eyepiece. The cap can have two ends, a first and open end which can slidably fit onto the eyepiece housing, and a second mounting end to mount the fixation light assembly.

While in FIG. 1 the fixation light assembly 40, 45 is not depicted as fully integral with the eyepiece housing 20 of the binocular indirect opthalmoscope assembly 10, it may, in some embodiments, be built into the manufactured apparatus. For example, the fixation light assembly may be built into the eyepiece housing 10 during the manufacture of the binocular indirect opthalmoscope assembly rather than, as depicted here, attached as an after-market type of device.

In another exemplary embodiment, the fixation light assembly 40, 45 can be affixed to the head mounting apparatus 35 of the binocular indirect opthalmoscope assembly 10, for example close to the ears of the examiner. Alternatively, the fixation light assembly 40, 45 can be likewise attached to other parts of the binocular indirect opthalmoscope assembly 10.

Figure 2:
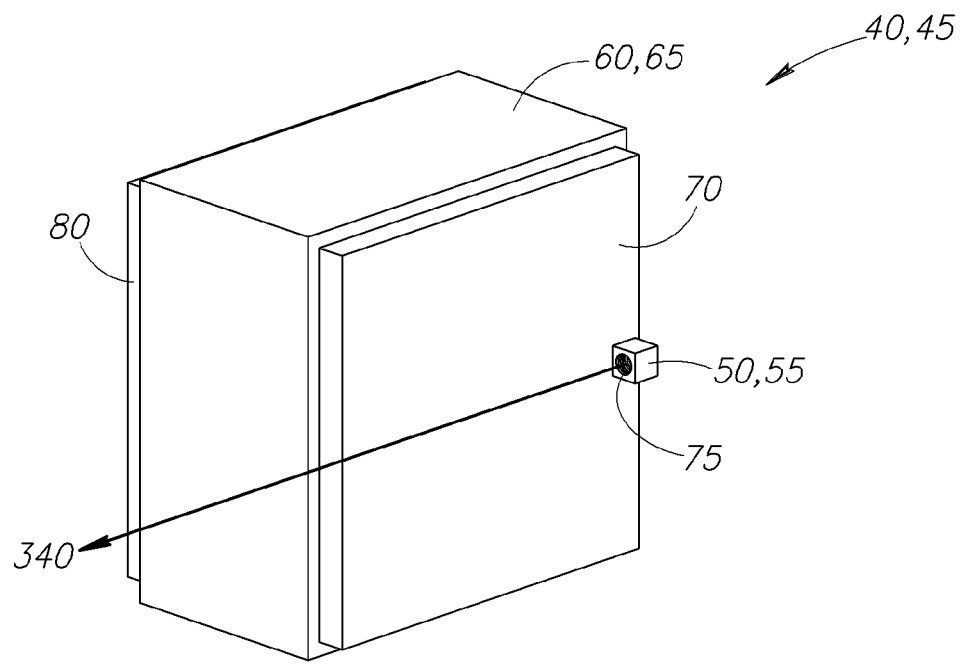
FIG. 2 shows a blown-up view of the binocular indirect opthalmoscope fixation light.

We refer now to FIG. 2, which shows the outer view of the binocular indirect opthalmoscope fixation light assemblies 40, 45. The fixation light housing 60, 65 can be, but is not limited to, a small rectangular box constructed of plastic. On a first side of the fixation light housing 60, 65, a printed circuit board 70 is mounted. A fixation light source 50, 55 is mounted at a right angle on the surface of the fixation light housing 60, 65, for example, a small right-angle surface mounted LED. In a preferred embodiment, the fixation light source 50, 55 can be mounted on the edge of an external surface of the printed circuit board 70 such that the light from an element 75 of the fixation light source 50, 55 projects forward and parallel to the printed circuit board 70. At a second and opposite side of the fixation light housing 60, 65, a self-adhesive layer 80 can be used to mount the fixation light housing 60, 65 onto the opthalmoscope housing 20. It is to be understood that when the fixation light assemblies 40, 45 are mounted onto either side of the eyepiece housing 20, either adjacent to the right eyepiece 25 or the left eyepiece 20, that the fixation light assemblies 40, 45 will be mirror images of each other, symmetrically arranged on either side of the eyepiece housing 20.

Figure 3:
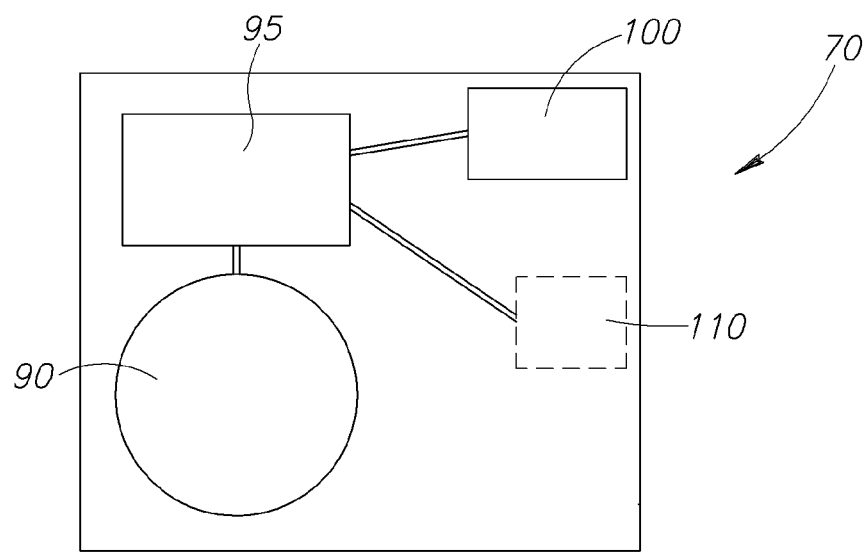
FIG. 3 shows a schematic view of the inner surface of the printed circuit board of the binocular indirect opthalmoscope fixation light.

FIG. 3, a schematic diagram illustrating one embodiment of a configuration of the inner surface of the printed circuit board 70. A battery power source 90 supplies power to a microprocessor 95, a motion/vibration sensor 100, and the footprint 110 of the attachment of the fixation light source 50, 55, which is in communication with the printed circuit board 70. The fixation light source 50, 55 is mounted on the opposite and external facing side of printed circuit board 70 (as shown in FIGS. 1 and 2). In operation, the vibration/movement sensor 100 senses a movement of the binocular indirect opthalmoscope assembly 10, and signals to the microprocessor 95 to turn on the light source 50, 55. A timing function of the microprocessor 95 maintains illumination of the light source 50, 55 for a set time interval, for example, a five minute period, and suppresses additional input during this period. After the set time interval, the microprocessor 95 turns off the light source 50, 55 and awaits another signal from the vibration/motion sensor 100.

FIG. 4 shows a schematic diagram of the binocular indirect fixation system 300 and the multiple pathways of light from the two fixation light sources 50, 55 during the use of the binocular indirect ophthalmoscope assembly 10. In one exemplary embodiment, as illustrated in FIG. 4, while examining the patient's right eye 120, the patient is asked to look at fixation light source 50, that can be, in this non-limiting example a colored or flashing light 50. This directs the line of sight 340A of the patient's left eye 125 and the line of sight 340 of the patient's right eye towards fixation light source 50. The first fixation light 50 is mounted on the fixation light housing 60 and attached to the right eyepiece 25 adjacent to the examiner's right eye 130. The second fixation light 55 is mounted on the fixation light housing 65 and attached to the left eyepiece 30 adjacent to the examiner's left eye 135. The patient cannot see the other, second light 55 with either eye because the path of light has been obscured by the fixation light housing 65 of the second light because of the rotation of the binocular indirect ophthalmoscope, and the viewing axis 310 towards the right eye 120 being examined. When binocular indirect ophthalmoscope assembly 10 is in this orientation, the fixation light 55 is blocked from the view of the patient by the fixation light housing 65. More specifically, the line of sight 320 of the patient's left eye 125 and the line of sight 330 of the patient's right eye 120 is obscured by the fixation light housing 65. Thus, while the examiner is examining the patients right eye 120, the only fixation light that the patient is able to see with either eye is the fixation light 50.

In use, the invention prevents confusion as to which light the patient should look at and assures that the direction of the patient's gaze is along the line of sight 340 and 340A, which insures that there is sufficient nasal rotation of the eye being examined (for example, patients right eye, FIG. 4 120) to orient the optic nerve and surrounding vessels in line with the viewing axis 310.

In operation the vibration/motion sensor 100 and timing circuit of microprocessor 95 in FIG. 3 allows the fixation light source 50, 55 to be activated automatically without having to be turned on and off. The binocular indirect opthalmoscope assembly 10 is preferably hung on the wall, thus allowing the examiner to readily utilize the apparatus when needed by picking it up and placing it on the head. In an alternative embodiment, this movement may be used to activate the vibration/motion sensor 100 in order to keep the fixation light source 50, 55 illuminated for a set time interval, for example five minutes, and/or a time sufficient for an examination using the binocular indirect opthalmoscope assembly 10. It is contemplated that other user selected time intervals can be chosen for different applications.

While the preferred embodiment of the invention has been illustrated and described, as noted above, many changes can be made without departing from the spirit and scope of the invention. For example, the fixation light assembly can be mounted in alternative positions on the binocular indirect opthalmoscope assembly; different light and power sources may be used; different materials may be used for the fixation light housing and pre- and post-manufacture adaptations may be made to mount the fixation light housing. Accordingly, the scope of the invention is not limited by the disclosure of the preferred embodiment. Instead, the invention should be determined entirely by reference to the claims that follow.

The invention claimed is:

1. A binocular indirect ophthalmoscope assembly comprising:
    an ophthalmoscope housing having a right and a left eyepiece for use by an examiner;
    an optical system contained in the ophthalmoscope housing for reflecting light along a optical viewing axis to each of the eyepieces;
    a binocular indirect fixation system, comprising;
        a first fixation light source configured to direct a beam of light to towards a patient, thereby causing the patient to gaze so as to place the optic nerve and surrounding retinal vessels of the eye under examination in the center of the examiner's view; and
        a second fixation light source configured to generate a beam of light that is hidden from view by the patient by at least one of the ophthalmoscope housing or a fixation light source housing when the patient is gazing at the first fixation light.

2. The binocular indirect ophthalmoscope assembly of claim 1, wherein the binocular indirect fixation system is removably mounted to the ophthalmoscope housing.

3. The binocular indirect ophthalmoscope assembly of claim 1, wherein the fixation light assemblies of the binocular indirect fixation system are mounted on either side of the ophthalmoscope housing.

4. The binocular indirect ophthalmoscope assembly of claim 1, wherein the fixation light housing has two sides, a first mounting side and a second fixation light source side.

5. The binocular indirect ophthalmoscope assembly of claim 4, wherein the first mounting side of the fixation light housing is mounted to the ophthalmoscope housing.

6. The binocular indirect ophthalmoscope assembly of claim 1, wherein the binocular indirect fixation system is activated by movement of the ophthalmoscope housing.

7. The binocular indirect ophthalmoscope assembly of claim 6, wherein the binocular indirect fixation system comprises a microprocessor in communication with a motion sensing device to turn on at least one fixation light source in response to motion detected by the motion sensing device.

8. The binocular indirect ophthalmoscope assembly of claim 1, wherein at least one of the fixation light sources is an LED.

9. The binocular indirect ophthalmoscope assembly of claim 1, wherein the binocular indirect fixation system is connected by direct wiring to a power source.

10. The binocular indirect ophthalmoscope assembly of claim 1, wherein the first and second fixation light sources are positioned adjacent to the right and left eyepieces, respectively, of the ophthalmoscope housing.

11. A binocular indirect fixation system for use in association with an indirect ophthalmoscope assembly to enable an examiner to examine a patient's retina, comprising:
    a first fixation light configured to direct a beam of light to towards a patient, thereby causing the patient to gaze so as to place the optic nerve and surrounding retinal vessels of the eye under examination in the center of the examiner's view; and
    a second fixation light configured to generate a beam of light that is hidden from view by the patient by at least one of an ophthalmoscope assembly housing or a fixation light source housing when the patient is gazing at the first fixation light.

12. The binocular indirect fixation system of claim 11, wherein the first and second fixation light sources are removably mounted to the indirect ophthalmoscope.

13. The binocular indirect fixation system of claim 11, wherein the fixation light housing has two sides, a first mounting side and a second fixation light source side.

14. The binocular indirect fixation system of claim 13, wherein the first mounting side of the fixation light housing is mounted to the indirect ophthalmoscope.

15. The binocular indirect fixation system of claim 11, wherein the binocular indirect fixation system is activated by movement.

16. The binocular indirect fixation system of claim 15, wherein the binocular indirect fixation system comprises a microprocessor in communication with a motion sensing device to turn on at least one fixation light source in response to motion detected by the motion sensing device.

17. The binocular indirect fixation system of claim 11, wherein at least one of the fixation light sources is an LED.

18. The binocular indirect fixation system of claim 11, wherein the binocular indirect fixation system is connected by direct wiring to a power source.

* * * * *